United States Patent
Ito (10) Patent No.: US 8,431,351 B2
(45) Date of Patent: Apr. 30, 2013

(54) **IMMUNOCHROMATOGRAPHY DETECTION OF MULTIDRUG-RESISTANT *STAPHYLOCOCCUS* AND DIAGNOSTIC KIT**

(75) Inventor: Hiromi Ito, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/229,159

(22) Filed: Sep. 9, 2011

(65) Prior Publication Data

US 2012/0064538 A1 Mar. 15, 2012

Related U.S. Application Data

(62) Division of application No. 12/097,460, filed as application No. PCT/JP2006/324905 on Dec. 14, 2006, now abandoned.

(30) Foreign Application Priority Data

Dec. 14, 2005 (JP) ................................. 2005-360984

(51) Int. Cl.
*G01N 33/53* (2006.01)
*G01N 33/542* (2006.01)
*G01N 33/554* (2006.01)

(52) U.S. Cl.
USPC .............. 435/7.1; 435/7.2; 435/7.32; 435/7.9

(58) Field of Classification Search ........................ None
See application file for complete search history.

(56) References Cited

U.S. PATENT DOCUMENTS

| | | | |
|---|---|---|---|
| 5,607,863 | A | 3/1997 | Chandler |
| 2002/0155623 | A1 | 10/2002 | Takahashi et al. |
| 2003/0044796 | A1 | 3/2003 | Neri et al. |
| 2005/0153370 | A1 | 7/2005 | Lakshmi et al. |
| 2008/0194013 | A1 | 8/2008 | Shida et al. |
| 2008/0220447 | A1 | 9/2008 | Purro et al. |

FOREIGN PATENT DOCUMENTS

| | | |
|---|---|---|
| EP | 1 596 199 A1 | 11/2005 |
| EP | 1 767 941 A1 | 3/2007 |
| JP | 10-78382 | 3/1998 |
| WO | WO 01-57531 A1 | 8/2001 |
| WO | WO 03/016903 | 2/2003 |
| WO | WO 2005/015217 A1 | 2/2005 |
| WO | WO 2005/121794 A1 | 12/2005 |

OTHER PUBLICATIONS

Supplementary European Search Report EP 06 83 4659 dated Jul. 2, 2009.
Matthias Cavassini et al., "Evaluation of MRSA-Screen a Simple Anti-PBP 2a Slide Latex Agglutination Kit, for Rapid Detection of Methicillin Resistance in *Staphylopcoccus aureus*", Journal of Clinical Microbiology, May 1999, vol. 37, No. 5, pp. 1591-1594.
Examination Report New Zealand Patent Application No. 569004 dated Mar. 12, 2010.
Non-Final Office Action U.S. Appl. No. 12/097,460 dated Oct. 27, 2010.
Non-Final Office Action U.S. Appl. No. 12/097,460 dated Jan. 28, 2011.
Sekiguchi et al., (Microbiology & Immunology vol. 39, No. 8, pp. 545-550, 1990).
Final Office Action U.S. Appl. No. 12/097,460 dated May 10, 2011.
Canadian Application No. 2,633,875, Office Action dated Nov. 19, 2012.

*Primary Examiner* — Albert Navarro
(74) *Attorney, Agent, or Firm* — Foley & Lardner LLP (57) ABSTRACT

This invention provides a immunochromatography detection device that can detect PBP2' produced specifically by a bacterium of multidrug-resistant *staphylococcus* with high sensitivity in a simple and rapid manner via immunochromatography detection to determine infection with multidrug-resistant *staphylococcus*, a diagnostic method using such detection device, and a diagnostic kit comprising such detection device.

12 Claims, 2 Drawing Sheets

IMMUNOCHROMATOGRAPHY DETECTION OF MULTIDRUG-RESISTANT *STAPHYLOCOCCUS* AND DIAGNOSTIC KIT

CROSS-REFERENCE TO RELATED APPLICATIONS

This application is a Divisional Application of U.S. application Ser. No. 12/097,460 filed Jun. 13, 2008; which is the U.S. National Phase of PCT/JP2006/324905 filed Dec. 14, 2006; which claims priority from Japanese Application No. 2005-360984 filed Dec. 14, 2005. The subject matter of each of the above-referenced applications is incorporated in entirety by reference.

TECHNICAL FIELD

The present invention relates to immunochromatography detection and a kit utilizing the same.

BACKGROUND ART

Staphylococci includes 40 or more bacterium types roughly classified into *Staphylococcus aureus* and coagulase-negative staphylococci (hereafter abbreviated to "CNS") from the clinical point of view. *Staphylococcus aureus* are regarded as pathogenic organisms and CNS are regarded as nonpathogenic organisms.

Infections are treated with the use of antibiotics. Since many staphylococci are drug-resistant, they are classified based on drug resistance from the clinical point of view.

Among *Staphylococcus aureus* that are clinically important pathogenic organisms, methicillin-resistant *Staphylococcus aureus* (MRSA) are *Staphylococcus aureus* that show resistance to β-lactam agents, including penicillin such as methicillin. Also, many such bacteria show resistance to many drugs such as aminoglycosides and macrolides. Thus, such bacteria are clinically regarded as multidrug-resistant *Staphylococcus aureus*. In contrast, *Staphylococcus aureus* showing sensitivity to methicillin are referred to as methcillin-sensitive *Staphylococcus aureus* (hereafter referred to as "MSSA").

*Staphylococcus aureus* produce a variety of toxins, including enterotoxin, toxic-shock syndrome toxin, hemolysin, and exfoliative toxin (Hideo IGARASHI: TSST-1, "*Shinshu to meneki* (Invasion and immunity)," 3, 3-10, 1994). Infection with such toxins would cause enteritis, pneumonia, dermatitis, organic failure, or the like, and serious infection may lead to death. When *Staphylococcus aureus* are isolated from a patient, accordingly, whether or not the bacterium is MRSA must be inspected as quickly as possible. In the event of MRSA infections, adequate drugs, such as vancomycin or arbekacin sulfate, which are regarded as being effective against MRSA, must be selected and administered to a patient.

Staphylococci other than *Staphylococcus aureus* are indigenous bacteria, and they are nonpathogenic to healthy individuals in general. When an organ transplant patient takes an immunosuppressant as a measure to prevent a postoperative infection or in the case of a so-called compromised patient with a weakened immune system due to an aging-induced weakened physical strength, however, opportunistic infections may occur.

Some staphylococci other than *Staphylococcus aureus* have acquired methicillin resistance or multidrug resistance, and these bacteria are collectively referred to as methicillin-resistant coagulase-negative staphylococci (hereafter abbreviated as "MRCNS") or multidrug-resistant coagulase-negative staphylococci, respectively. As with the case of MRSA, drugs that are effective against MRCNS are limited if a compromised patient is infected therewith. Thus, MRCNS has been a medical problem.

MRSA and MRCNS are collectively referred to as multidrug-resistant *staphylococcus*.

The drug resistance of MRSA or MRCNS is known to result from expression of a new enzyme, PBP2', in addition to four types of penicillin-binding proteins (i.e., PBP1, PBP2, PBP3, and PBP4) that crosslink murein chains, which are constitutional elements of the cell wall of staphylococci and which synthesize the cell wall (Utsui, Y., and Yokota, T.: Role of an altered penicillin-binding protein in methicillin- and cephem-resistant *Staphyloccus aureus*., Antimicrobial Agents and Chemotherapy, 28, 397-403, 1985). PBP1 to PBP4 proteins that staphylococci possess in common are inactivated as cell-wall-synthesizing enzymes by penicillin antibiotics, which are substrate analogues, and bacteria eventually die when synthesis of cell walls becomes unfeasible. However, MRSA and MRCNS express a new cell-wall-synthesizing enzyme, PBP2', which exhibits little affinity to β-lactam antibiotic substances, i.e., which would not be inactivated thereby. MRSA and MRCNS are considered to proliferate by altering roles in cell wall synthesis. Most MRSA and MRCNS acquire mechanisms of resistance to other antibiotics and become multidrug-resistant bacteria that are resistant to many antibiotics. Such bacteria are regarded as multidrug-resistant staphylococci instead of staphylococci having resistance merely to β-lactam antibiotics.

General techniques for separating and identifying staphylococci involve the use of nasal cavity swabs, pharyngeal swabs, sputum, blood, pus, stool, or other samples as clinical samples, and isolation culture thereof with the use of an agar medium or liquid agar medium is performed. When cultured in an agar medium, colonies suspected of being staphylococci are selected from among the grown colonies and further subjected to pure culture, and staphylococci or *Staphylococcus aureus* are identified via microscopic visualization of Gram-stained images or biochemical character tests of coagulase production capacity or mannitol degradation capacity. When cultured in a liquid medium, a culture solution is sowed on an agar medium and cultured therein for colony isolation, and colonies suspected of being staphylococci are also subjected to pure culture followed by identification. The bacteria that have been identified as the *Staphylococcus aureus* or staphylococci are subjected to a drug-sensitivity test or the like, and whether or not a bacterium of interest is MRSA, MSSA, or MRCNS is determined based on test results. A drug-sensitivity test is generally carried out by culture, such as a dilution technique or a disk sensitivity test. Such drug sensitivity test is known to require a culture duration of 16 to 24 hours (it would take 3 or more days from separation of clinical samples to determination if both isolation culture and pure culture are conducted) and to produce differences in test results due to, for example, the concentration of bacteria, culture temperature, medium composition, or drug to be used. Thus, a person who conducts such test is required to be highly experienced with the procedure.

In recent years, a method that detects the mecA gene encoding PBP2', which is a main body of a drug-resistant mechanism, via pure culture, isolation culture, or directly from a clinical sample via PCR to evaluate antibody resistance based on the conditions of the mecA gene carried in the analyte bacterium has been developed. However, the fact that a bacterium carries the mecA gene does not always mean the expression of antibiotic resistance, and some bacteria have not acquired resistance even though they carry such gene.

As described above, production of PBP2' plays a key role in the expression of multidrug resistance, and detection of PBP2' from staphylococci can be a useful means for learning whether or not a bacterium of interest has acquired resistance.

PBP2' produced specifically by bacteria of the multidrug-resistant *staphylococcus*, including MRSA, is detected by an antigen-antibody-reaction-based immunological means, such as Western blotting, radioimmunoassay, or a slide latex agglutination test (JP Patent No. 3638731). Such methods of detecting PBP2', however, suffer from the following problems. Western blotting is complicated in terms of procedure, and it is difficult to rapidly process many samples. Radioimmunoassay is not practical from the viewpoint of routine testing, since it involves the use of a radioisotope, it requires BF separation involving separating an antigen-antibody complex from other non-binding antigens or antibodies during assay, and it requires several hours to complete assay due to the presence of a denaturing agent used for extracting an antigen from the bacterium in the reaction system. The slide latex agglutination test requires detection from axenic bacteria due to false-positive reactions caused by contaminating bacteria (e.g., false-positive reactions due to nonspecific reactions) and low sensitivity. Thus, culture must be conducted at least twice, i.e., isolation culture and pure culture, which in turn requires 2 to 3 days to complete the determination, it increases the cost for mediums for pure culture, and it may cause a false-positive reaction due to agglutination after the determination time, even though such time can be as short as 3 minutes. It is also laborious due to the need of centrifugation for separating a PBP2'-containing supernatant from cell-wall-derived pieces at the time of pretreatment of extracting PBP2' from the bacterium, which may contaminate the environment of the laboratory, it involves complicated procedures such as transfer of a supernatant after centrifugation via pipetting, and it involves boiling. Accordingly, a method that can rapidly detect PBP2' produced specifically by a bacterium of multidrug-resistant *staphylococcus* with high specificity and sensitivity has been awaited as a replacement for conventional detection techniques.

DISCLOSURE OF THE PRESENT INVENTION

Object to be Attained by the Invention

The present invention is intended to provide an immunochromatography detection device that can detect PBP2' produced specifically by a bacterium of multidrug-resistant *staphylococcus* with high sensitivity in a simple and rapid manner via immunochromatography detection to determine infection with multidrug-resistant *staphylococcus*, a diagnostic method using such detection device, and a diagnostic kit comprising such detection device.

Means for Attaining the Object

The present inventors have conducted concentrated studies regarding a method for extracting PBP2' from a bacterium of multidrug-resistant *staphylococcus* and assaying the same in a simple and rapid manner without complicated procedures. They succeeded in assaying PBP2' in a simple manner with the use of an immunochromatography detection device using a reagent that is a labeled antibody binding specifically to PBP2' and a capture reagent that can specifically bind to and capture a complex of PBP2' and the labeled reagent. Further, they discovered that PBP2' could be extracted and assayed without the need for complicated centrifugation or other means by treating a sample with an alkaline solution before assay, neutralizing the same, and applying the same to the immunochromatography detection device. Further, they discovered that assay can be carried out without causing a false-positive reaction by applying a surfactant such as an ampholytic surfactant to a capture reagent site of the immunochromatography detection device on which the capture reagent has been immobilized. This has led to the completion of the present invention.

More specifically, the present invention is as follows.

[1] A method for detecting a bacterium that produces a cell-wall-synthesizing enzyme, PBP2', comprising detection of a cell-wall-synthesizing enzyme, PBP2', via immunochromatography detection based on an antigen-antibody reaction.

[2] The method for detecting a bacterium that produces a cell-wall-synthesizing enzyme, PBP2', according to [1], which involves the use of an immunochromatography detection device comprising on a sheet-like solid-phase support: a sample supply site to which a sample solution deduced to contain a bacterium producing a cell-wall-synthesizing enzyme, PBP2' or a solution deduced to contain PBP2' released from the cell wall via sample pretreatment is supplied; a labeled reagent site that holds a reagent, which is a labeled antibody binding specifically to PBP2', in a manner such that the reagent is able to spread across the solid-phase support; and a capture reagent site on which a capture reagent capable of specifically binding to and capturing a complex of PBP2' and the labeled reagent has been immobilized.

[3] The method for detecting a bacterium that produces a cell-wall-synthesizing enzyme, PBP2', according to [1] or [2], wherein PBP2' comes into contact with the labeled reagent at a site separated from a solid-phase support in advance, and a sample-reagent mixture comprising a sample solution deduced to contain a bacterium producing a cell-wall-synthesizing enzyme, PBP2' or a solution deduced to contain PBP2' released from the cell wall via sample pretreatment and the labeled reagent that is a labeled antibody binding specifically to PBP2' is supplied to the sample supply site.

[4] The method for detecting a bacterium that produces a cell-wall-synthesizing enzyme, PBP2', according to [2] or [3], wherein the labeled reagent is an insoluble carrier to which an antibody is bound.

[5] The method for detecting a bacterium that produces a cell-wall-synthesizing enzyme, PBP2', according to any one of [2] to [4], wherein the capture reagent site comprises an ampholytic surfactant, an anionic surfactant, and/or a nonionic surfactant.

[6] The method for detecting a bacterium that produces a cell-wall-synthesizing enzyme, PBP2', according to any one of [2] to [5], wherein the capture reagent site comprises a sulfobetaine-type surfactant.

[7] The method for detecting a bacterium that produces a cell-wall-synthesizing enzyme, PBP2', according to [5] or [6], wherein an anion having a high ionization tendency is added to a sample solution deduced to contain a bacterium producing a cell-wall-synthesizing enzyme, PBP2', or a solution deduced to contain PBP2' released from the cell wall via sample pretreatment prior to supply of such solution to a sample supply site.

[8] The method for detecting a bacterium that produces a cell-wall-synthesizing enzyme, PBP2', according to [7], wherein the anion having a high ionization tendency is at least one anion selected from the group consisting of a chloride ion, a bromide ion, and an iodide ion.

[9] The method for detecting a bacterium that produces a cell-wall-synthesizing enzyme, PBP2', according to any one of [5] to [8], wherein a cation having a high ionization tendency is added to a sample solution deduced to contain a bacterium producing a cell-wall-synthesizing enzyme, PBP2', or a solution deduced to contain PBP2' released from the cell wall via sample pretreatment prior to supply of such solution to a sample supply site.

[10] The method for detecting a bacterium that produces a cell-wall-synthesizing enzyme, PBP2', according to [9], wherein the cation having a high ionization tendency is at least one cation selected from the group consisting of a potassium ion, a calcium ion, a sodium ion, and a magnesium ion.

[11] The method for detecting a bacterium that produces a cell-wall-synthesizing enzyme, PBP2', according to any one of [1] to [11], which comprises a step of pretreating a sample via alkaline treatment or neutralization.

[12] The method for detecting a bacterium that produces a cell-wall-synthesizing enzyme, PBP2', according to [11], wherein the alkaline treatment is carried out using an aqueous solution of alkali metal hydroxide or carbonate or an aqueous solution of alkaline earth metal hydroxide or carbonate.

[13] The method for detecting a bacterium that produces a cell-wall-synthesizing enzyme, PBP2', according to [12], wherein the pH of the aqueous solution of alkali metal hydroxide or carbonate or the aqueous solution of alkaline earth metal hydroxide or carbonate is 11 or higher.

[14] The method for detecting a bacterium that produces a cell-wall-synthesizing enzyme, PBP2', according to [12] or [13], wherein the concentration of the alkali metal hydroxide or carbonate or alkaline earth metal hydroxide or carbonate is between 0.01N and 1.0N.

[15] The method for detecting a bacterium that produces a cell-wall-synthesizing enzyme, PBP2', according to any one of [11] to [14], wherein the aqueous solution after alkali treatment is neutralized with a buffer.

[16] The method for detecting a bacterium that produces a cell-wall-synthesizing enzyme, PBP2', according to any one of [1] to [15], wherein the sample supply site comprises glass fibers.

[17] The method for detecting a bacterium that produces a cell-wall-synthesizing enzyme, PBP2', according to any one of [1] to [16], wherein the bacterium producing a cell-wall-synthesizing enzyme, PBP2', is a multidrug-resistant *staphylococcus*.

[18] An immunochromatography detection device for detecting a bacterium producing a cell wall synthesizing enzyme, PBP2', comprising on a sheet-like solid-phase support: a sample supply site to which a sample solution deduced to contain a bacterium producing a cell-wall-synthesizing enzyme, PBP2' or a solution deduced to contain PBP2' released from the cell wall via sample pretreatment is supplied; a labeled reagent site that holds a reagent, which is a labeled antibody binding specifically to PBP2', in a manner such that the reagent is able to spread across the solid-phase support; and a capture reagent site on which a capture reagent capable of specifically binding to and capturing a complex of PBP2' and the labeled reagent has been immobilized, the capture reagent site comprising an ampholytic surfactant, an anionic surfactant, and/or a nonionic surfactant.

[19] The immunochromatography detection device for detecting a bacterium producing a cell wall synthesizing enzyme, PBP2', according to [18], wherein the capture reagent site comprises a sulfobetaine-type surfactant.

[20] The immunochromatography detection device for detecting a bacterium producing a cell wall synthesizing enzyme, PBP2', according to [18] or [19], wherein the sample supply site comprises glass fibers.

[21] The immunochromatography detection device for detecting a bacterium producing a cell wall synthesizing enzyme, PBP2', according to any one of [18] to [20], wherein the bacterium producing a cell-wall-synthesizing enzyme, PBP2', is a multidrug-resistant *staphylococcus*.

[22] A kit for detecting a bacterium producing a cell-wall-synthesizing enzyme, PBP2', comprising: the immunochromatography detection device for detecting a bacterium producing a cell wall synthesizing enzyme, PBP2', according to any one of [18] to [21]; and an anion or cation solution having a high ionization tendency to be added to a sample solution deduced to contain a bacterium producing a cell-wall-synthesizing enzyme, PBP2', or a solution deduced to contain PBP2' released from the cell wall via sample pretreatment.

[23] The kit for detecting a bacterium producing a cell-wall-synthesizing enzyme, PBP2', according to [22], wherein the anion having a high ionization tendency is at least one anion selected from the group consisting of a chloride ion, a bromide ion, and an iodide ion.

[24] The kit for detecting a bacterium producing a cell-wall-synthesizing enzyme, PBP2', according to [22], wherein the cation having a high ionization tendency is at least one cation selected from the group consisting of a potassium ion, a calcium ion, a sodium ion, and a magnesium ion.

[25] The kit for detecting a bacterium producing a cell-wall-synthesizing enzyme, PBP2', according to any one of [22] to [24], which further comprises an alkali solution for alkali treatment of a sample with alkali and a buffer for neutralization.

[26] The kit for detecting a bacterium producing a cell-wall-synthesizing enzyme, PBP2', according to [25], wherein the alkali solution is an aqueous solution of alkali metal hydroxide or carbonate or an aqueous solution of alkaline earth metal hydroxide or carbonate.

[27] The kit for detecting a bacterium producing a cell-wall-synthesizing enzyme, PBP2', according to [26], wherein the pH of the aqueous solution of alkali metal hydroxide or carbonate or the aqueous solution of alkaline earth metal hydroxide or carbonate is 11 or higher.

[28] The kit for detecting a bacterium producing a cell-wall-synthesizing enzyme, PBP2', according to [26] or [27], wherein the concentration of the alkali metal hydroxide or carbonate or alkaline earth metal hydroxide or carbonate is between 0.01N and 1.0N.

[29] The kit for detecting a bacterium producing a cell-wall-synthesizing enzyme, PBP2', according to any one of [22] to [28], wherein the bacterium producing a cell-wall-synthesizing enzyme, PBP2', is a multidrug-resistant *staphylococcus*.

Effects of the Invention

Use of the immunochromatography detection device of the present invention enables detection of PBP2' with high sensitivity. This then enables testing with one colony after isolation culture. Consequently, whether or not a bacterium of interest is MRSA or MRCNS can be evaluated via a single operation of culture in 1 day after separation thereof from the clinical sample. This can remarkably reduce testing duration and the cost of mediums used for pure culture. Further, blood (liquid) culture that is carried out for testing MRSA bacteremia or septicemia enables direct detection from a positive medium. This enables initiation of effective treatment at an early stage, which leads to reduction of treatment duration.

Also, centrifugation becomes unnecessary by imparting filtration effects to a sample application member on a support on which an antibody has been immobilized. Thus, sanitary laboratory conditions can be maintained.

A capture site of the immunochromatography detection device may be impregnated with a surfactant, so that binding of fractured bacteria other than antigens to the labeled reagent and/or the capture site can be prevented; i.e., false-positive reactions can be prevented, and sensitivity can be improved. This makes a previously necessary boiling procedure in the process of bacterium pretreatment unnecessary.

This description includes part or all of the contents as disclosed in the description and/or drawings of Japanese Patent Application No. 2005-360984, which is a priority document of the present application.

Description of Reference Numerals

1: A sample supply site
2: A labeled reagent site
3: A capture reagent (capture antibody) site
4: A control site
5: A solid-phase support (nitrocellulose membrane)
6: An absorption site (absorbent pad)
7: A top laminate or housing

BEST MODES FOR CARRYING OUT THE INVENTION

Hereafter, the present invention is described in detail.

The present invention relates to an immunochromatography detection device that can detect PBP2' that is present specifically in a bacterium producing a cell-wall-synthesizing enzyme, PBP2', such as a multidrug-resistant *staphylococcus*, with high sensitivity in a simple and rapid manner via immunochromatography detection to determine infection with a bacterium producing a cell-wall-synthesizing enzyme, PBP2', such as a multidrug-resistant *staphylococcus*, and a diagnostic kit. The term "sample" used herein refers to a solution deduced to contain a bacterium producing a cell-wall-synthesizing enzyme, PBP2', and more specifically, a solution deduced to contain a multidrug-resistant *staphylococcus* bacterium, including a solution of bacteria suspended therein, which was prepared by smearing a growth medium, such as blood agar medium, normal agar medium, heart infusion agar medium, brain heart infusion agar medium, soybean/casein/digest agar medium, chocolate agar medium, egg-yolk-containing mannitol salt agar medium, or MRSA selection medium, with an analyte substance, such as urine, pus, spinal fluid, secreted material, or puncture fluid obtained from a suspected patient and culturing the same under aerobic conditions at 35° C. to 37° C. for 18 hours or longer, and a culture solution resulting from shake culture in liquid culture medium, blood culture medium, or the like under aerobic conditions at 35° C. to 37° C. for 18 hours or longer. The term also refers to an extract deduced to contain PBP2' released from the cell wall due to pretreatment of such a suspension of bacteria. The "bacterium producing a cell-wall-synthesizing enzyme, PBP2'" includes multidrug-resistant *staphylococcus*, and the "multidrug-resistant *staphylococcus*" includes multidrug-resistant *Staphylococcus aureus* (MRSA) and multidrug-resistant coagulase-negative staphylococci (MRCNS). A solution of an analyte substance, such as urine, pus, spinal fluid, secreted material, puncture fluid, or another sample obtained from a suspected patient suspended directly in physiological saline or phosphate buffer can also be a sample. From the viewpoint of detection sensitivity, use of a solution containing bacteria cultured in the above-described manner is preferable.

Figure 1:
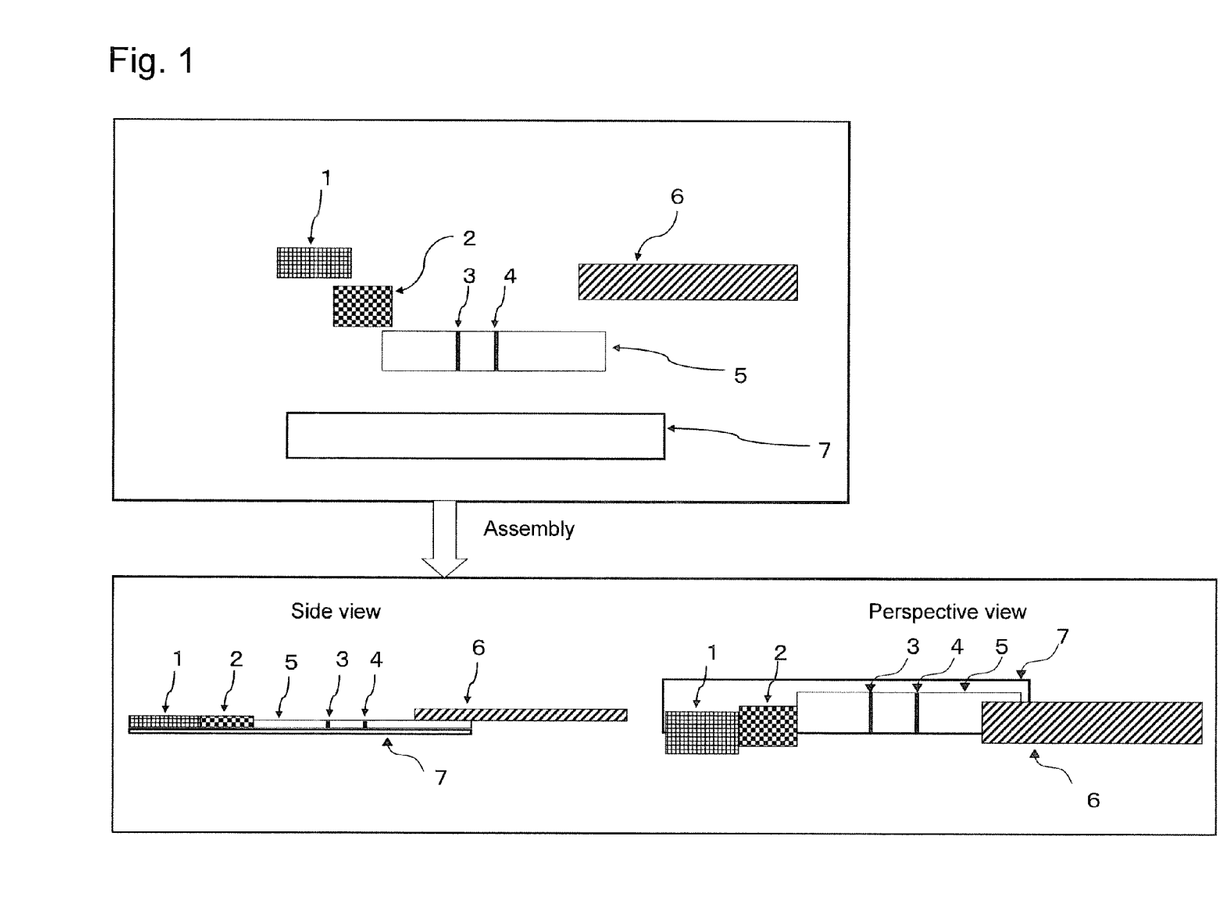
FIG. 1 shows an embodiment of the detection device of the present invention comprising a labeled reagent site.
Figure 2:
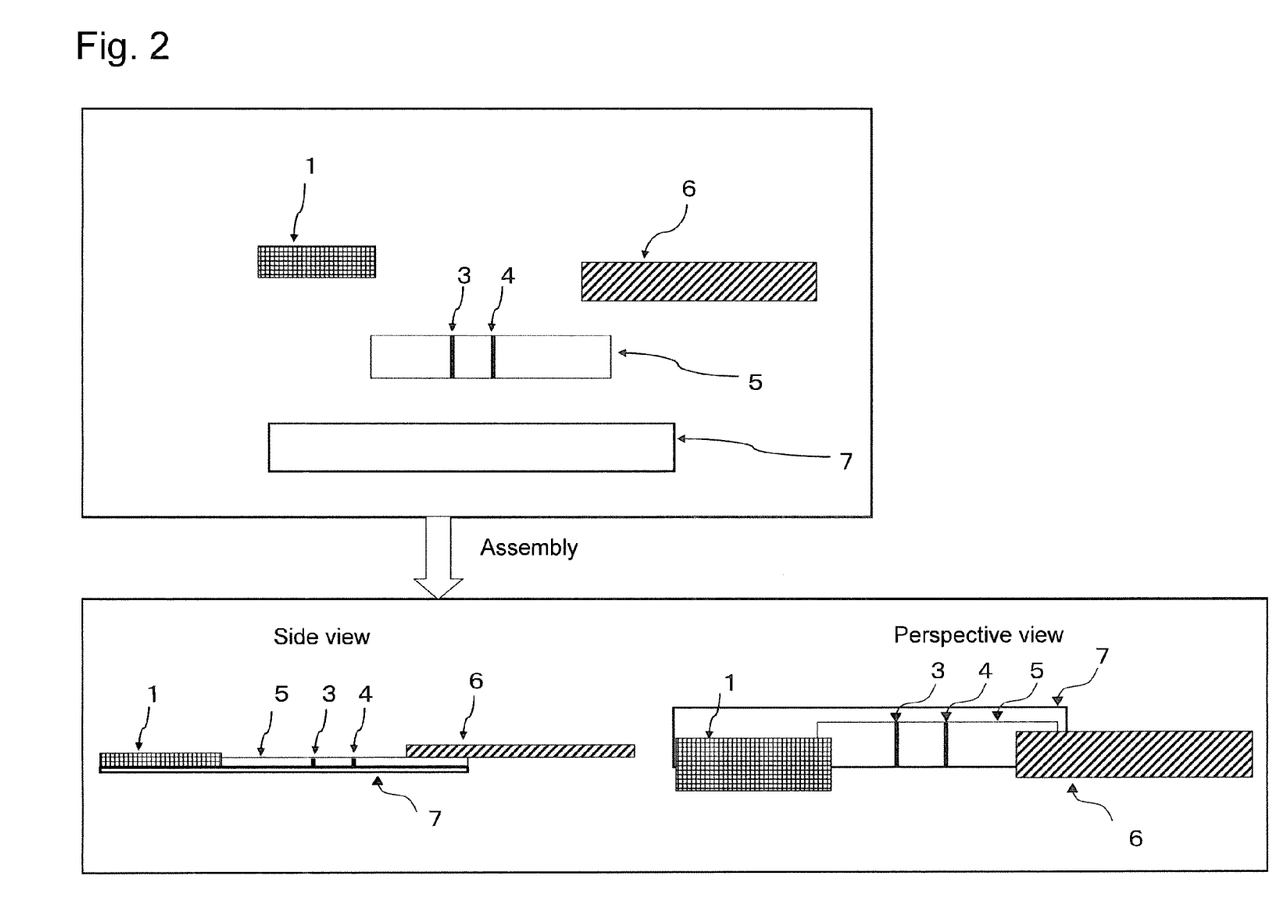
FIG. 2 shows an embodiment of the detection device of the present invention comprising no labeled reagent site.

The immunochromatography detection device of the present invention is an immunochromatography test piece. For example, such device is composed as shown in FIG. 1. Such device comprises on sheet-like solid-phase support; a sample supply site 1 to which a sample is supplied; a labeled reagent site 2 that holds a reagent, which is a labeled antibody binding specifically to PBP2', in a manner such that the reagent is able to spread across the solid-phase support; and a capture reagent site 3 on which a capture reagent capable of specifically binding to and capturing a complex of PBP2' and the labeled reagent has been immobilized. When a sample is supplied to the sample supply site 1, the sample passes through the a labeled reagent site 2 and the capture reagent site 3 in that order. In the present invention, a mixture of a sample and a reagent that is a labeled antibody binding specifically to PBP2' may be supplied to the sample supply site 1. In such a case, the labeled reagent site 2 on the solid-phase support may be omitted (FIG. 2). When the mixture of a sample and a reagent that is a labeled antibody binding specifically to PBP2' is to be supplied to the sample supply site 1, PBP2' contained in the sample comes into contact with the labeled reagent at a site separated from a solid-phase support in advance. The phrase "an analyte comes into contact with a labeled reagent at a site separated from a solid-phase support in advance" refers to conditions such that the labeled reagent is not contained on the solid-phase support, or it is in contact with the solid-phase support, and such that a liquid is not included at a site that can communicate with the solid-phase support, such as a sample supply site, of the immunochromatography detection device. In such a case, an analyte comes into contact with the labeled reagent in advance, apart from the solid-phase support or a site that is in contact with the solid-phase support.

The immunochromatography detection device of the present invention may further comprise a control reagent and an absorption site. A control reagent is not particularly limited. For example, a substance to which an antibody in a labeled reagent binds may be used. A control reagent may be immobilized at a site downstream of the capture reagent site. In FIG. 1, a control site 4 corresponds to such site. An absorption site is capable of absorbing a liquid such that it absorbs a sample that has passed through the capture site to regulate the flow of the sample. Such site may be provided at the lowermost site of the detection device. In FIG. 1, an absorption site 6 corresponds to such site. For example, an absorption site made of paper may be used as an absorbent pad.

In the immunochromatography detection device of the present invention, a sample supply site may be constituted by an end of a solid-phase support as is, or it can be constituted by a member different from a solid-phase support. In the case of the latter constitution, a sample supply site is provided in contact with a solid-phase support, so that a solution can spread and migrate to the solid-phase support with the aid of capillary flow, in order that a sample supply site first absorbs a sample, or a mixture of a sample and a labeled reagent, and then supplies the absorbed sample or mixture to the solid-phase support. Examples of members other than a solid-phase support include, but are not limited to, members composed of natural or synthetic polymers of nitrocellulose, cellulose acetate, nylon, polyethersulfone, polyvinyl alcohol, polyester, glass fiber, polyolefin, cellulose, or polystyrene and a mixture of such substances.

The "labeled reagent" of the immunochromatography detection device of the present invention is a conjugate of an antibody binding specifically to PBP2' and an adequate label substance. Examples of a label substance include metal colloids, such as gold colloid, nonmetal colloids, such as selenium colloid, and insoluble substances such as colored resin particles. In the present invention, such label substances are occasionally referred to as "insoluble carriers." Preferably, insoluble carriers are negatively charged. In general, a labeled reagent is impregnated with a member different from a solid-phase support, dried, and then placed at a site continuous with the solid-phase support. Alternatively, the solid-phase support may be directly applied with the labeled reagent and then dried. When the sample reaches a labeled reagent site containing a labeled reagent, the labeled reagent is dissolved in the sample, and the resulting solution can then be spread across the solid-phase support. Specifically, a labeled reagent is held at a labeled reagent site in a manner extensible on the support.

The capture reagent of the immunochromatography detection device of the present invention is an antibody binding specifically to PBP2', a capture reagent site can specifically bind to and capture a complex of PBP2' and a labeled reagent, and a complex of a labeled reagent/PBP2'/a capture reagent is then formed. In general, a capture reagent is prepared via direct applying of a solid-phase support, followed by drying, although the method of preparation is not limited thereto. A member other than a solid-phase support may be impregnated with a capture reagent and then dried, and the resultant may be placed on the solid-phase support. A method for immobilizing a capture reagent on a solid-phase support is not limited to adsorption. Immobilization may be carried out by a conventional technique, such as chemical binding with the use of a functional group such as an amino or carboxyl group.

An antibody to be used as a capture reagent may be same as an antibody to be used as a labeled reagent. When there is only one site that binds to such substance in PBP2', however, a complex of a labeled reagent/PBP2'/a capture reagent would not be formed. In such a case, accordingly, a capture reagent is required to bind to a site of PBP2' that is different from a site to which a labeled reagents binds.

A solid-phase support may be of any substance, provided that a sample can be absorbed by such support and fluidized via capillary phenomenon. For example, a support is selected from the group consisting of a natural or synthetic polymer of nitrocellulose, cellulose acetate, nylon, polyethersulfone, polyvinyl alcohol, polyester, glass fiber, polyolefin, cellulose, or polystyrene and a mixture of such substances. A solid-phase support is preferably strip-shaped.

The cell-wall-synthesizing enzyme, PBP2', that is produced specifically by a bacterium of multidrug-resistant *staphylococcus* is present on a cell membrane located inside the cell wall. Pretreatment of breaking or melting the cell wall of multidrug-resistant *staphylococcus* facilitates a capture reagent and a labeled reagent to recognize PBP2'. As an extraction reagent for breaking or melting the cell wall of multidrug-resistant *staphylococcus*, a cell-wall-digesting enzyme or a given surfactant having bactericidal action, such as a given cationic surfactant or ampholytic surfactant, is known. Use of such reagents is difficult because such reagents are expensive and strongly inhibit an antigen-antibody reaction at the time of immunochromatography detection, and for other reasons. Thus, use of a dilute alkaline solution is preferable as an extraction reagent for PBP2' at the time of immunochromatography detection in the present invention. Specific examples thereof include an aqueous solution of 0.01N to 1.0N alkali metal hydroxide or carbonate and an aqueous solution of 0.01N to 1.0N alkaline earth metal hydroxide or carbonate. The pH of such dilute alkaline solution is preferably 11 or higher.

When a solution containing bacteria is pretreated with an dilute alkaline solution as described above, an antigen-antibody reaction would be inhibited if a pH remains at 11 or higher after the pretreatment. Thus, neutralization of an alkaline solution is required. A neutralization solution is not particularly limited, and examples thereof include phosphate buffer, Tris buffer, and Good's buffer, such as MES, Bis-Tris, ADA, PIPES, ACES, MOPSO, BES, MOPS, TES, HEPES, DIPSO, TAPSO, POPSO, HEPPSO, EPPS, Tricine, Bicine, or TAPS, exhibiting buffering capacity at the optimal pH of the reaction system, i.e., between 6 and 8, for immunochromatography detection. In the present invention, pretreatment of bacteria is a process of extracting a bacterium producing a cell-wall-synthesizing enzyme, PBP2', and more particularly, PBP2' as an antigen by exposing a solution of bacteria deduced to contain multidrug-resistant *staphylococcus* to alkaline conditions. "Pretreatment" also refers to a process of neutralizing alkaline conditions. Pretreatment may be carried out by adding an alkaline solution to a sample solution comprising bacteria for alkalinization and then adding a neutralizing solution thereto. Alternatively, bacteria collected with the use of a platinum loop or cotton swab may be suspended directly in an alkaline solution, and a neutralizing solution may then be added. The amounts of such solutions to be added are not limited, and such amounts may be determined so as to bring the pH of the neutralized sample solution to around 6 to 9. Also, a sample supply site may be impregnated with a neutralizing solution in advance and then dried.

In the present invention, the solution of bacteria may be pretreated and then neutralized, additives, such as salt, a surfactant, a protein, a polymer, an acidic compound, and a basic compound, may be added thereto, the resultant may be thoroughly mixed, and the sample may then be supplied to the sample supply site of the immunochromatography detection device. These additives can enhance sensitivity of an antigen-antibody reaction and can reduce false-positive reactions (e.g., false-positive reactions due to nonspecific reactions). Further, such additives may be added to the aforementioned dilute alkaline solution or neutralizing solution in advance to reduce procedural steps.

When detection of multidrug-resistant *staphylococcus* is intended, substances derived from non-multidrug-resistant staphylococci (MSSA or MSCNS) or bacteria other than staphylococci may occasionally bind to antibodies (i.e., as a labeled reagent and a capture reagent) and may show false-positive results. Thus, with the use of a PBP2' detection reagent used for latex agglutination assay, false-positive causative agents, such as protein A, that are present on the cell wall of *Staphylococcus aureus* exhibiting the capacity for binding to IgG had to be inactivated by boiling a solution of bacteria in the presence of an alkaline reagent, remnants after cell fracturing after centrifugation had to be eliminated, and the supernatant after centrifugation had to be used for testing. Via immunochromatography detection according to the present invention, a capture reagent site of the immunochromatography detection device may be impregnated with a surfactant to inhibit binding of a false-positive causative agent to a capture antibody, without inactivating the false-positive causative agent by boiling. An ampholytic surfactant, an anionic surfactant, or a nonionic surfactant is preferable, and including one of them may be sufficient. Inhibition of binding of a false-positive causative agent to a capture antibody with the aid of a surfactant is considered to result from masking of a site of an antibody to which a false-positive causative agent binds by a surfactant. Accordingly, surfactants with larger molecular weights and/or greater numbers of cyclic structures are considered to be more effective. When any of the following nonionic surfactants are used, for example, false-positive results originating from non-multidrug-resistant *Staphylococcus aureus* that is not multidrug-resistant are more inhibited compared with the case where no surfactant was added: a nonionic surfactant having a molecular weight of 646 and a single 6-membered ring structure (tradename: Tx100; Nacalai Tesque); an ampholytic surfactant having a molecular weight of 364 without a 6-membered ring structure (tradename: SB3-14; Calbiochem); an ampholytic surfactant having a molecular weight of 615, three 6-membered ring structures, and a single 5-membered ring structure (tradename: CHAPS; DOJINDO LABORATORIES); or a nonionic surfactant having a molecular weight of 878, and three 6-membered ring structures, and a single 5-membered ring structure (tradename: BIGCHAP, DOJINDO LABORATORIES). The effects of inhibition attained with the use of CHAPS and BIGCHAP were greater than those attained with the use of Tx100 and SB3-14. Accordingly, the molecular weight of a surfactant is considered to be preferably 300 or higher, and more preferably 600 or higher, and a surfactant is considered to preferably comprise a greater number of cyclic structures, such as 6-membered rings. For the purpose of inhibiting false-positive reactions, use of a surfactant that is charged in the same manner as with the case of an insoluble carrier is preferable. When an insoluble carrier is a negatively charged latex or gold colloid, it is preferable that a surfactant also be negatively charged.

A false-positive reaction resulting from protein A present in the cell wall of *Staphylococcus aureus* is of particularly serious concern. Protein A strongly binds to the Fc region of immunoglobulin G. Antibodies that specifically recognize PBP2' are used as labeled reagents and capture reagents. Antibodies may be immunoglobulin G or immunoglobulin M, without particular limitation. When immunoglobulin G is used, such antibody is used while eliminating the Fc region, and a capture reagent region is combined with the aforementioned surfactant. Thus, a false-positive reaction caused by protein A can be avoided. The Fc region can be easily eliminated with the use of a known degrading enzyme, such as pepsin or papain.

Protein G contained in the cell wall of group G Streptococcus also binds specifically to the Fc region of immunoglobulin G. When a sample solution contains group G Streptococcus, accordingly, protein G may nonspecifically react with a labeled reagent or a capture reagent, as with the case of protein A. Such false-positive reaction can also be avoided in the above-described manner.

Among surfactants to be applied to the capture reagent site, properties of an ionic surfactant are particularly affected by the concentration of anions or cations in the solution that passes through the capture reagent region. This necessitates determination of the optimal concentration of anions or cations in the solution in accordance with the type, concentration, properties, or other conditions of a surfactant to be used. Examples of anions include a chloride ion, a bromide ion, and an iodide ion having a high ionization tendency. Examples of cations include a potassium ion, a calcium ion, a sodium ion, and a magnesium ion having a high ionization tendency. In this case, a plurality of anions or cations may be used.

Detection sensitivity can be improved by adding a surfactant containing a sulfobetaine region to a capture reagent site, which is the method according to the present invention. Since PBP2' could not be detected with high sensitivity with the use of a PBP2' detection reagent via latex agglutination assay, the cell wall had to be broken via boiling of a solution of bacteria in the presence of an alkaline reagent in order to completely extract PBP2'. According to the present invention, detection sensitivity is improved with the addition of a surfactant containing a sulfobetaine region, which enabled detection of PBP2' with high sensitivity even when elution of PBP2' is incomplete in the absence of boiling. Boiling in the presence of an alkaline reagent would cause PBP2' degradation, or would cause desensitization via denaturation of an antibody recognition site due to structural changes; however, detection sensitivity can be advantageously maintained with the absence of boiling.

Examples of surfactants each containing a sulfobetaine region include CHAPS, CHAPSO, myristylsulfobetaine (SB3-14), and dodecyl dimethyl ammonio butane sulfonate (DDABS).

A surfactant for inhibiting binding of the false-positive causative agent to a capture antibody, and a surfactant for improving sensitivity are added to a capture reagent in advance when a capture reagent is to be immobilized at a capture reagent site. Either or both of a surfactant for inhibiting binding of the false-positive causative agent to a capture antibody and a sulfobetaine-type surfactant capable of improving sensitivity may be used. Alternatively, a surfactant for inhibiting binding of the false-positive causative agent to a capture antibody may be a sulfobetaine-type surfactant, and sensitivity can be improved in such a case.

Further, the method of the present invention can produce the effect of inhibiting binding of a false-positive causative agent to a capture antibody and the effect of improving sensitivity by adding a surfactant containing a sulfobetaine region having a molecular weight of preferably 300 or higher, and more preferably 600 or higher, to a capture reagent site. Specifically, CHAPS and SB3-14 are preferable, with CHAPS being particularly preferable. A plurality of surfactants may be added to the capture reagent site.

When an anion or cation is added as described above, such anion or cation may be added to a sample solution deduced to contain multidrug-resistant *staphylococcus* or a sample solution deduced to contain PBP2' released from the cell wall via sample pretreatment.

The method of the present invention further includes a method of preventing a false-positive causative agent from reaching the capture reagent site, thereby preventing influences of such false-positive causative agent. For example, a false-positive causative agent may be eliminated at a site upstream of the capture reagent site in the device of the present invention. As a means for eliminating a false-positive causative agent, a sample supply site of the immunochromatography detection device preferably comprises glass fibers. A bacteria-derived false-positive causative agent is adsorbed by glass fibers, which inhibits the false-positive causative agent from passing through the capture reagent. This can consequently inhibit a false-positive reaction.

The method of the present invention is a detection method based on an antigen-antibody reaction using a cell-wall-synthesizing enzyme, PBP2', as an antigen and an antibody reacting therewith. If a cell-wall-synthesizing enzyme, PBP2', is present in the sample, accordingly, PBP2' can be detected by the method of the present invention. In general, a cell-wallsynthesizing enzyme, PBP2', is produced specifically by a multidrug-resistant *staphylococcu*, and is present specifically in such bacterium.

At present, the existence of PBP2'-producing bacteria other than multidrug-resistant *staphylococcus* is not known. In the present description, the term "multidrug-resistant *staphylococcus*" is occasionally used as a specific example instead of the term "a bacterium producing a cell-wall-synthesizing enzyme, PBP2'." Such use is not intended to limit the bacterium to "a multidrug-resistant *staphylococcus*." This term can be read as "a bacterium producing a cell-wall-synthesizing enzyme, PBP2'" within the scope that allows the method of the present invention to be implemented. That is, bacteria producing PBP2' other than multidrug-resistant *staphylococcus* can be detected by the method of the present invention. Further, bacteria each containing a cell-wall-synthesizing enzyme, PBP2', can be detected by the method of the present invention. In general, a cell-wall-synthesizing enzyme, PBP2', is considered to be present specifically on a cell membrane inside the cell wall of a multidrug-resistant *staphylococcus*. The method of the present invention involves the use of a PBP2' extraction reagent used for pretreatment of breaking or melting the cell membrane. Accordingly, bacteria each comprising a cell-wall-synthesizing enzyme, PBP2', inside the cell wall can be effectively detected by the method of the present invention.

EXAMPLES

Hereafter, the present invention is described in greater detail with reference to the following examples, although the present invention is not limited thereto.

Example 1

Detection of PBP2' in MRSA via Immunochromatography Detection (FIG. 1)

(1) Preparation and Drying of Latex Particles Sensitized with Antibody

An anti-PBP2' monoclonal antibody was treated with pepsin in accordance with conventional technique to obtain F(ab')2. The resultant was subjected to sensitization of 0.4 μm of latex particles, and the resulting solution was sprayed on an unwoven polystyrene fabric. The resultant was then dried under reduced pressure for 1 hour in a decompression device to prepare a dry latex antibody pad. The pad was cut at intervals of 4 mm for use and used as a labeled site 2.

(2) Preparation of Immunochromatography Detection Device

A second anti-PBP2' monoclonal antibody having a recognition site different from that of the anti-PBP2' monoclonal antibody used for latex sensitization was treated with pepsin in accordance with a conventional technique to obtain F(ab') 2. The resultant was diluted with a citrate buffer (pH 6) containing 0.075% CHAPS, the resultant was applied to a nitrocellulose membrane (solid-phase support 5), and the membrane was thoroughly dried (capture reagent site 3). As a control reagent, anti-mouse IgGs was applied to a nitrocellulose membrane in the same manner and thoroughly dried (control site 4).

A capture reagent site 3 and a solid-phase support 5 including a control site 4 were provided on a hydrophobic sheet 7, and a labeled reagent site 2, a glass fiber as a sample supply site 1, and a filter paper as an absorption site 6 were provided at any positions.

(3) Pretreatment of Sample

*Staphylococcus aureus* (14 bacteria) were cultured on blood agar medium at 35° C. overnight, and a loopful of culture was suspended directly in 0.2N NaOH. Similarly, a colony was picked up and then suspended in 100 μl of 0.2N NaOH. The resultant was then neutralized with 50 μl of 0.6M Tris-HCl buffer containing a nonionic surfactant, bovine serum albumin, and rabbit IgG.

(4) Assay

The immunochromatography detection device was introduced into a 1.5-ml tube containing a solution after pretreatment of samples, color development of a capture reagent 3 was evaluated with the naked eye ten minutes later, and the capture reagent that had developed color was identified as positive. The reagent that had not developed color was identified as negative.

(5) Drug Sensitivity Test

Bacteria cultured in the same manner as in (3) were suspended in a sterilized 0.9% sodium chloride solution, and the absorbance at 578 nm of the solution was adjusted to 0.3. The resulting solution was sowed on Muller-Hinton agar medium containing 6 μg/ml oxacillin and 4% sodium chloride, culture was conducted at 35° C. for 24 hours, the bacteria that had grown were determined to be MRSA, and the bacteria that had not grown were determined to be MSSA.

(6) Results

The results are shown in Table 1.

TABLE 1

| | | Drug sensitivity | | |
|---|---|---|---|---|
| | | MRSA | MSSA | Total |
| | | One loopful | | |
| Present invention | MRSA | 4 | 0 | 4 |
| | MSSA | 0 | 10 | 10 |
| | Total | 4 | 10 | 14 |
| | | One colony | | |
| Present invention | MRSA | 4 | 0 | 4 |
| | MSSA | 0 | 10 | 10 |
| | Total | 4 | 10 | 14 |

As is apparent from Table 1, the positive concordance rate between MRSA and MSSA is 100% (4/4), and the negative concordance rate therebetween is 100% (10/10). This indicates that the concordance rate as a whole is 100% (14/14). These results represent the superiority of present invention to conventional techniques.

Example 2

Effect of Addition of Surfactant to Capture Reagent Site (1) Preparation and Drying of Latex Particles Sensitized with Antibody The latex particles prepared in Example 1 were used.

(2) Preparation of Immunochromatography Detection Device

The device was prepared in the same manner as in Example 1. In this case, an device comprising a capture reagent site and 0.05% CHAPS, Tx100, SB3-14, BIGCHAP, and DTAC (dodecyl trimethyl ammonium chloride) added thereto and an device comprising no such substances were prepared and used.

(3) Pretreatment of Sample

A bacterium that had been evaluated as being drug-sensitive, i.e., MSSA, and a bacterium that had been evaluated as being drug-resistant, i.e., MRSA, via the drug sensitivity test were cultured in the same manner as in Example 1. Two and three loopfuls of MSSA and a loopful of MRSA were picked up and then pretreated.

(4) Assay

An MSSA was tested in the same manner as in Example 1 without dilution. Further, the MRSA was subjected to two-step dilution with a mixture comprising 0.2N NaOH and 0.6M Tris HCl buffer (containing a nonionic surfactant, bovine serum albumin, and rabbit IgG) at 2:1, and 150 µl thereof diluted at least 1024-fold was tested in the same manner as in Example 1.

(5) Results

The results attained with the device comprising a surfactant added to a capture reagent site and the results attained with the device comprising no surfactant were compared. The results attained with the use of MSSA are shown in Table 2. The negative results are represented by "−," and the degree of false-positive reaction are represented by the number of "+"s. The results attained with the use of MRSA are shown in Table 3. A negative result is represented by "−," and a positive result is represented by "+."

TABLE 2

| | MSSA | | | | | |
|---|---|---|---|---|---|---|
| | Without addition | Tx 100 | CHAPS | SB3-14 | BIGCHAP | DTAC |
| MSSA (2 loopfuls) | + | − | − | − | − | + |
| MSSA (3 loopfuls) | ++ | + | − | + | − | ++ |

When a surfactant was not added and a cationic surfactant, DTAC, was added, a false-positive result was attained with 2 loopfuls of MSSA. When Tx 100 or SB3-14 having a relatively small molecular weight was added, 3 loopfuls thereof caused a false-positive reaction, although the degree thereof was not as strong as that attained when a surfactant was not added or when DTAC was added. When CHAPS or BIGCHAP having a relatively large molecular weight was added, 2 and 3 loopfuls thereof yielded a negative result.

As is apparent from Table 2, addition of a nonionic surfactant, i.e., Tx100 or BIGCHAP, or an ampholytic surfactant, i.e., CHAPS or SB3-14, to a capture reagent site can inhibit a false-positive reaction originating from MSSA. Also, CHAPS or BIGCHAP comprising a large number of cyclic structures and having a large molecular weight can more effectively inhibit a false-positive reaction. These results demonstrate the superiority of the addition of a surfactant to a capture reagent site.

TABLE 3

| | MRSA | | | | | |
|---|---|---|---|---|---|---|
| | Without addition | Tx 100 | CHAPS | SB3-14 | BIGCHAP | DTAC |
| 1:1024 | + | + | + | + | + | + (false-positive) |
| 1:2048 | − | − | + | + | − | + (false-positive) |
| 1:4096 | − | − | − | − | − | + (false-positive) |

Detection sensitivity was improved with the addition of CHAPS or SB3-14 to a capture reagent site. The results attained with the addition of DTAC were considered to constitute a false-positive.

As is apparent from Table 3, the addition of a sulfobetaine-type surfactant, i.e., SB3-14 or CHAPS, to a capture reagent site can improve sensitivity, compared with cases in which no surfactant was added or a non-sulfobetaine-type surfactant, i.e., Tx100 or BIGCHAP, was added. These results demonstrate superiority of the addition of a sulfobetaine-type surfactant to a capture reagent site.

The results of Example 2 demonstrate that CHAPS particularly shows satisfactory effects of inhibiting a false-positive reaction and those of improving sensitivity and that CHAPS is thus particularly useful.

Example 3

Detection of PBP2' in MRCNS via Immunochromatography Detection (1) Preparation and Drying of Latex Particles Sensitized with Antibody The latex particles prepared in Example 1 were used.

(2) Preparation of Immunochromatography Detection Device

The device was prepared in the same manner as in Example 1.

(3) Pretreatment of Sample

Among staphylococci that exhibit properties of staphylococci via gram staining and that had been evaluated to be positive via a catalase test and to be negative via a coagulase test, two bacteria that had been evaluated as being methicillin-sensitive, i.e., MSCNS, via a drug sensitivity test and a bacterium that had been evaluated as being methicillin-resistant, i.e., MRCNS, via a drug sensitivity test were cultured in the same manner as in Example 1, and a loopful thereof was picked and then subjected to pretreatment.

(4) Assay

Assay was conducted in the same manner as in Example 1.

(5) Drug Sensitivity Test

Test was conducted in the same manner as in Example 1.

(6) Results

The results are shown in Table 4. The results of the drug sensitivity test are represented as follows: S: sensitivity; R: resistance; +: positive result; and −: negative result.

TABLE 4

| | Drug sensitivity test | Present invention |
|---|---|---|
| Strain A | S | − |
| Strain B | S | − |
| Strain C | R | + |

The two strains that had been evaluated as being sensitive, i.e., MSCNS, via the drug sensitivity test showed negative results, and a strain that had been evaluated as being resistant, i.e., MRCNS, via the drug sensitivity test showed positive results.

All publications, patents, and patent applications cited herein are incorporated herein by reference in their entirety.

The invention claimed is:

1. A method for detecting a bacterium that produces a cell-wall-synthesizing enzyme, PBP2', comprising detection of PBP2' via immunochromatography detection based on an antigen-antibody reaction,
   (i) which uses an immunochromatography detection device comprising on a sheet-like solid-phase support:
      (a) a sample supply site to which a sample solution is supplied, which sample solution is deduced to contain a bacterium producing PBP2' or a solution deduced to contain PBP2' released from the cell wall via sample pretreatment;
      (b) a labeled reagent site that holds a reagent, which is a labeled antibody binding specifically to PBP2', in a manner such that the reagent is able to spread across the solid-phase support; and
      (c) a capture reagent site on which a capture reagent capable of specifically binding to and capturing a complex of PBP2' and the labeled reagent has been immobilized, the capture reagent site comprising a sulfobetaine-type surfactant, and
   (ii) which comprises supplying to the sample supply site the sample solution and then evaluating at the capture reagent site the formation of a complex of a labeled reagent/PBP2'/a capture reagent.

2. The method for detecting a bacterium that produces a cell-wall-synthesizing enzyme, PBP2', according to claim 1, wherein PBP2' comes into contact with the labeled reagent at a site separated from a solid-phase support in advance, and a sample-reagent mixture comprising a sample solution deduced to contain a bacterium producing a cell-wall-synthesizing enzyme, PBP2' or a solution deduced to contain PBP2' released from the cell wall via sample pretreatment and the labeled reagent that is a labeled antibody binding specifically to PBP2' is supplied to the sample supply site.

3. The method for detecting a bacterium that produces a cell-wall-synthesizing enzyme, PBP2', according to claim 1, wherein the labeled reagent is an insoluble carrier to which an antibody is bound.

4. The method for detecting a bacterium that produces a cell-wall-synthesizing enzyme, PBP2', according to claim 1, wherein an anion selected from the group consisting of a chloride ion, a bromide ion and an iodide ion is added to a sample solution deduced to contain a bacterium producing a cell-wall-synthesizing enzyme, PBP2', or a solution deduced to contain PBP2' released from the cell wall via sample pretreatment prior to supply of such solution to a sample supply site.

5. The method for detecting a bacterium that produces a cell-wall-synthesizing enzyme, PBP2', according to claim 2, wherein a cation selected from the group consisting of a potassium ion, a calcium ion and a magnesium ion is added to a sample solution deduced to contain a bacterium producing a cell-wall-synthesizing enzyme, PBP2', or a solution deduced to contain PBP2' released from the cell wall via sample pretreatment prior to supply of such solution to a sample supply site.

6. The method for detecting a bacterium that produces a cell-wall-synthesizing enzyme, PBP2', according to claim 1 which comprises a step of pretreating a sample via alkaline treatment or neutralization.

7. The method for detecting a bacterium that produces a cell-wall-synthesizing enzyme, PBP2', according to claim 6, wherein the alkaline treatment is carried out using an aqueous solution of alkali metal hydroxide or carbonate or an aqueous solution of alkaline earth metal hydroxide or carbonate.

8. The method for detecting a bacterium that produces a cell-wall-synthesizing enzyme, PBP2', according to claim 7, wherein the pH of the aqueous solution of alkali metal hydroxide or carbonate or the aqueous solution of alkaline earth metal hydroxide or carbonate is 11 or higher.

9. The method for detecting a bacterium that produces a cell-wall-synthesizing enzyme, PBP2', according to claim 7, wherein the concentration of the alkali metal hydroxide or carbonate or alkaline earth metal hydroxide or carbonate is between 0.01 N and 1.0 N.

10. The method for detecting a bacterium that produces a cell-wall-synthesizing enzyme, PBP2', according to claim 6, wherein the aqueous solution after alkali treatment is neutralized with a buffer.

11. The method for detecting a bacterium that produces a cell-wall-synthesizing enzyme, PBP2', according to claim 1, wherein the sample supply site comprises glass fibers.

12. The method for detecting a bacterium that produces a cell-wall-synthesizing enzyme, PBP2', according to claim 1, wherein the bacterium producing a cell-wall-synthesizing enzyme, PBP2', is a multidrug-resistant *staphylococcus*.

* * * * *